(12) United States Patent
Stecker et al.

(10) Patent No.: US 6,620,129 B2
(45) Date of Patent: Sep. 16, 2003

(54) ENLARGEABLE MULTIFUNCTIONAL DEVICES

(76) Inventors: Eric C. Stecker, 1607 Abbott Ave., Ann Arbor, MI (US) 48103; Philip P. Stecker, 3400 N. French Rd., Appleton, WI (US) 54911; Barbara L. Stecker, 3400 N. French Rd., Appleton, WI (US) 54911

(*) Notice: Subject to any disclaimer, the term of this patent is extended or adjusted under 35 U.S.C. 154(b) by 0 days.

(21) Appl. No.: 09/946,418

(22) Filed: Sep. 5, 2001

(65) Prior Publication Data

US 2003/0009130 A1 Jan. 9, 2003

Related U.S. Application Data

(60) Provisional application No. 60/303,643, filed on Jul. 9, 2001.

(51) Int. Cl.[7] .......................... A61M 29/00; A61M 37/00
(52) U.S. Cl. ..................................... 604/107; 604/95.04
(58) Field of Search ................. 604/104–109, 604/27, 264, 95.04, 96.01; 606/191–194, 198, 167, 170

(56) References Cited

U.S. PATENT DOCUMENTS

| | | | |
|---|---|---|---|
| 5,203,773 A | * 4/1993 | Green | 604/104 |
| 5,235,966 A | 8/1993 | Jamner | 128/20 |
| 5,275,610 A | 1/1994 | Eberback | 606/198 |
| 5,339,803 A | 8/1994 | Mayzels et al. | 128/20 |
| 5,353,784 A | 10/1994 | Nady-Mohamed | 128/20 |
| 5,358,496 A | 10/1994 | Ortiz et al. | 606/198 |
| 5,443,449 A | * 8/1995 | Buelna | 604/105 |
| 5,556,376 A | 9/1996 | Yoon | 604/15 |
| 5,800,394 A | 9/1998 | Yoon et al. | 604/101 |
| 5,993,473 A | 11/1999 | Chan et al. | 606/192 |

OTHER PUBLICATIONS

The sages Manual Fundamentals of Laparoscopy and GI Endoscopy, edited by Carol E.H. Scott–Corner, Spinger Pub., 1999.

* cited by examiner

*Primary Examiner*—Michael J Hayes
(74) *Attorney, Agent, or Firm*—Medlen & Carroll, LLP

(57) ABSTRACT

The present invention relates generally to multifunctional devices for performing suction, irrigation, and manipulation at an internal site in a subject, and more particularly to enlargeable multifunctional devices for performing such functions while avoiding obstruction during conventional and endoscopic surgery. The present invention eliminates many of the problems associated with malleable tissue obstruction during surgery by providing the ability to deploy and retract a guard (e.g. enlargeable section) to create an area free of tissue interference.

15 Claims, 5 Drawing Sheets

ENLARGEABLE MULTIFUNCTIONAL DEVICES

The present application claims priority to Provisional Application Serial No. 60/303,643, filed Jul. 9, 2001, herein incorporated by reference.

FIELD OF THE INVENTION

The present invention relates generally to multifunctional devices for performing suction, irrigation, and manipulation at an internal site in a subject, and more particularly to enlargeable multifunctional devices for performing such functions while avoiding obstruction during conventional and endoscopic surgery.

BACKGROUND OF THE INVENTION

There are two fundamental types of surgery, conventional and endoscopic surgery. Conventional surgery generally involves a relatively large incision with direct visualization (e.g. the "naked eye") of the area being operated upon. Examples of conventional surgery include heart and bowel surgeries. Endoscopic surgery involves indirect visualization of the operative field with a small camera. Endoscopic surgery is generally done by way of multiple small incisions through which a camera and instruments are inserted. The instruments perform their functions inside the body but are operated by use of their handles outside the body. Examples of endoscopic surgery include endoscopic appendix or gallbladder removal. Endoscopic surgery can also be done through existing, natural orifices (e.g. certain prostate surgeries).

A surgeon uses mechanical devices to assist in performing a variety of interventions within the surgical field during an operation. Three functions generally performed by such mechanical devices include direct tissue manipulation, irrigation, and suction. Direct tissue manipulation may include, but is not limited to, cutting, stitching, cauterizing, injecting, and scraping. Irrigation may include washing the surgical area with fluids (often directed with a tube and/or nozzle). Irrigation is employed as the area of interest within the operative field can become contaminated or can be obscured from visualization by blood or debris. Suction is employed as irrigation fluids and bodily fluids collect in the operative field and need to be removed. There are various devices that currently fulfill these functions. Their use is sometimes impeded, however, when malleable tissue such as fat or intestine surrounds the area of interest and obstructs visualization and/or operation of the device. Below are examples of the limitations of currently used devices.

Currently utilized direct tissue manipulation devices come in many different designs. These devices do not have a feature to intrinsically hold malleable tissue away from the tip of the instrument. This function is served by an assistant's hands or a separate device. This can make surgery particularly difficult during small incision conventional surgery or any endoscopic surgery.

Currently utilized suction devices contain a tube of fixed diameter (see, e.g., FIG. 1). These devices have an opening and/or perforations on the sides of the barrel through which fluid flows and is removed from the operative field. However, during endoscopic surgery (or other types of surgery), the ability to retract tissue out of the operative field is constrained by the limited number of introducer ports through which extra instruments can be placed. Thus, suction devices are frequently operated in close proximity to malleable tissue such as fat or intestine. This leads to frequent obstructions of the suction ports which require the surgeon to disengage the tissue from the device in order to resume suctioning of fluid. Disengaging the tissue from the suction device uses valuable operating room time and distracts from the primary tasks of the operation.

Currently utilized irrigation devices simply have a tube through which fluid is expelled into the operative field for cleansing or visualization purposes. Like the other two examples, malleable tissue can obstruct the end of the instrument.

What is needed are multifunctional devices capable of performing functions at an internal site in a subject (e.g. suction, irrigation, tissue manipulation) while avoiding obstruction from malleable tissue.

SUMMARY OF THE INVENTION

The present invention relates generally to multifunctional devices for performing suction, irrigation, and manipulation at an internal site in a subject, and more particularly to enlargeable multifunctional devices for performing such functions while avoiding obstruction during conventional and endoscopic surgery.

In some embodiments, the present invention provides multifunctional devices (e.g. for performing at least one function at an internal site in a subject), comprising; an elongate member with a plurality of openings defining an enlargeable section, wherein the enlargeable section comprises a plurality of walls, and wherein the enlargeable section is movable between a non-enlarged position, and an enlarged position. In preferred embodiments, the enlarged position creates a chamber in the elongate member. In particular embodiments, the enlarged position is any position of the enlargeable section that has a cross-sectional dimension greater than the enlarged section when in the non-enlarged position. In certain embodiments, the enlargeable section, when moved from the non-enlarged position to the enlarged position, is capable of pushing bodily tissue outward (e.g. the walls of the enlargeable section are capable of pushing bodily tissue away from the elongate member axis).

In other embodiments, the present invention provides multifunctional devices (e.g. for performing at least one function at an internal site in a subject comprising; an elongate member with a plurality of openings defining an enlargeable section, wherein the enlargeable section comprises a plurality of walls, and wherein the enlargeable section is movable between a non-enlarged position, and an enlarged position, wherein the enlarged position forms a chamber in the elongate member, and b) a sleeve member enclosing at least a portion of the elongate member, the sleeve member being moveable between a first position along the elongate member that fully encloses the enlargeable section, and a second position along the elongate member that at most partially encloses the enlargeable section. In particular embodiments, the sleeve member enclosing at least a portion of the elongate member may be pushed distally around the enlargeable section to transfer the location of maximal suction and/or irrigation forces toward the distal end of the device.

In certain embodiments, the present invention provides methods for constructing a multifunctional device, comprising; a) providing an elongate member, and b) generating a plurality of openings in the elongate member such that an enlargeable section is formed in the elongate member, the enlargeable section comprising a plurality of walls and being moveable between a non-enlarged position and an enlarged position. In preferred embodiments, the enlarged position creates a chamber in the elongate member.

In other embodiments, the present invention provides methods for constructing a multifunctional device, comprising; a) providing; i) an elongate member, and ii) a sleeve member configured for enclosing at least a portion of the elongate member; and b) generating a plurality of openings in the elongate member such that an enlargeable section is formed in the elongate member, the enlargeable section comprising a plurality of walls and being moveable between a non-enlarged position and an enlarged position, wherein the enlarged position creates a chamber in the elongate member; and c) inserting the elongate member into the sleeve member such that the sleeve member is moveable between a first position along the elongate member that fully encloses the enlargeable section, and a second position along the elongate member that at most partially encloses the enlargeable section.

In some embodiments, the present invention provides methods for performing at least one function at an internal site in a subject, comprising; a) providing; i) a multifunctional device comprising an elongate member with a plurality of openings defining an enlargeable section, wherein the enlargeable section comprises a plurality of walls, and wherein the enlargeable section is movable between a non-enlarged position, and an enlarged position, wherein the enlarged position creates a chamber in the elongate member, and ii) a subject comprising a body opening; and b) inserting the multifunctional device through the body opening into an internal site in the subject with the enlargeable section in the non-enlarged position. In preferred embodiments, the method further comprises step c) moving the enlargeable section from the non-enlarged position to the enlarged position. In certain embodiments, the methods of the present invention are part of an endoscopic surgery or endoscopic procedure. In some embodiments, the moving step is accomplished by pushing the distal end of the device against a solid surface in the subject (e.g. against tissue in the subject).

In other embodiments, the device further comprises a sleeve member, and the moving step is accomplished by moving the sleeve member to a position such that it does not enclose the enlargeable section. In other embodiments, the body opening is an incision in the body of the subject. In some embodiments, the body opening is a natural orifice in the body of the subject. In particular embodiments, the sleeve member enclosing at least a portion of the elongate member may be pushed downward around the enlargeable section to transfer the location of maximal suction and/or irrigation forces toward the proximal end of the device.

In certain embodiments, the elongate member is configured for transmitting fluid (e.g. into and/or out of a surgical site). In some embodiments of the present invention, the elongate member is configured for suctioning. In other embodiments, the elongate member is configured for irrigation.

In particular embodiments, the elongate member comprises a tube (e.g. a cylindrical, hollow member with openings at both ends). In some embodiments, the tube comprises plastic (e.g., polyethylene, polypropylene, polystyrene, polyvinyl chloride, nylon, polyacetal, polyphenylene oxide, polytetrafluoethylene, polyethylene teraphthalate, polybutylene terephthalate, phenolic urea formaldehyde, melamine formaldehyde, polyester, and combinations thereof). In some embodiments, the elongate member is at least 1 centimeter in length (e.g. at least 1 centimeter, or at least 2 centimeters, or at least 3 centimeters). In certain embodiments, the elongate member is at least 5 centimeters in length (e.g. at least 5 centimeters, or at least 10 centimeters). In other embodiments, the elongate member is at least 12, or at least 15, or at least 18, or at least 20 centimeters in length. In particular embodiments, the elongate member is no more than 5 centimeters in length (e.g. no more than 5 centimeters, or no more than 3 centimeters, or no more than 2 centimeters).

In some embodiments, the elongate member has a primary cross-sectional dimension (e.g., a cross-sectional dimension that is present throughout at least 50 percent of the length of the elongate member). In certain embodiments, the primary cross-sectional dimension is present throughout at least 60 percent, or at least 70 percent, or at least 80 percent, or at least 90 percent, or at least 95 percent, or at least 99 percent of the elongate member. In preferred embodiments, the cross-sectional dimension of the elongate member is uniform throughout its length. In certain embodiments, the primary cross-sectional dimension is a diameter value ranging between 2 millimeters and 15 millimeters (e.g., approximately 2 mm, 3 mm, 8 mm, 12 mm, or 14 mm). In other embodiments, the primary cross-sectional dimension is a diameter value ranging between 4 millimeters and 10 millimeters (e.g. approximately 4 mm, 6 mm, 8 mm or 10 mm).

In particular embodiments, the elongate member comprises a distal tip. In further embodiments, the enlargeable section of the elongate member has a bulging midsection shape. In other embodiments, the elongate member has a distal end and a proximal end. In certain embodiments, distal end of the elongate member is configured to be inserted in a body opening of a subject (e.g. during endoscopic surgery). In some embodiments, the proximal end of the elongate member is configured to remain outside the body (e.g., during endoscopic surgery such that the device may be manipulated by a user, such as a surgeon). In other embodiments, the enlargeable section is located in the distal end of the elongate member. In still other embodiments, the multifunctional device further comprises a handle. In particular embodiments, the handle is located in, or attached to, the proximal end of the elongate member.

In certain embodiments, the plurality of walls are separated by at least one of the plurality of openings (e.g. at least 1, 2, 3, 4, 5, 6, 7, 8, or 9 of the plurality of openings). In other embodiments, at least one of the plurality of walls is at least 1 millimeter in length (e.g., at least 1, 2, 3, 4, 5, or 6 millimeters in length).

In some embodiments, at least one of the plurality of openings in the elongate member is a longitudinal opening. In further embodiments, the at least one longitudinal opening is at least 1 millimeter in length (e.g. at least 1 mm, 2 mm, 3 mm, 4 mm, 5 mm, or 6 mm in length). In certain embodiments, the plurality of openings comprises at least three separate openings (e.g. at least 4, or 5, or 6, or 7, or 8, or 9, or 15, or 20 separate openings). The plurality of openings of the present invention may be of any shape or size. In some embodiments, the openings are longitudinal, diamond, zig-zag shape, regular or irregularly shaped, and allow adjustment of the chamber shape and/or volume.

In certain embodiments, the enlargeable section, when in the enlarged position, has a cross-sectional dimension at least 1.5 times larger than the enlarged section when in the non-enlarged position (e.g. at least 1.5 times larger, or at least 2 times larger, or at least 3 times larger, or at least 4 times larger). In some embodiments, the chamber has a volume of at least 5 cubic centimeters (e.g., at least 6 cc, 7 cc, 8 cc, 9 cc, or at least 10 cc).

In preferred embodiments, at least a portion of the enlargeable section is enclosed by media (e.g., an expandable membrane, such as GORE-TEX ePTFE membranes, made by W. L. Gore & Associates, Inc., Elkton, Md.). In particularly preferred embodiments, the media is biocompatible. In other preferred embodiments, the media further comprises a therapeutic agent, including, but not limited to, antibiotics, anticoagulants, steroids, and combinations thereof. In some embodiments, the media is permeable to liquid. In other embodiments, the media (e.g. latex) is impermeable to liquid. In still other embodiments, the media is partially permeable to liquids. In other embodiments, the media comprises perforations (e.g. that allow fluid to pass).

In certain embodiments, the multifunctional device further comprises an adjustment device. In other embodiments, at least a portion of the adjustment device is within the elongate member. In some embodiments, the adjustment device is configured for changing the shape of the chamber. In preferred embodiments, the adjustment device is configured for moving the enlargeable section from the non-enlarged position to the enlarged position, or vice-versa. In other embodiments, the adjustment device comprises a handle component (e.g. such that user can operate the adjustment device from outside the body of a patient).

In some embodiments, the multifunctional devices of the present invention further comprise an inner utility member. In particular embodiments, the inner utility member comprises a rod or rod-like member. In certain embodiments, the inner utility member is configured for transmitting fluid (e.g. irrigation or suction, or both). In other embodiments, the inner utility member is configured for attachment to a tissue manipulator tip (or the distal end of the inner utility member forms a tissue manipulator tip). In some embodiments, the multifunctional device further comprises a tissue manipulator tip (e.g. connected to the inner utility member).

In certain embodiments, the enlargeable section of the elongate member comprises a spring member. In some embodiments, the spring member is configured to move the enlargeable section to the enlarged position. In other embodiments, the spring member is configured to move the enlargeable section to the non-enlarged position. In other embodiments, the enlargeable section has passive spring action (e.g. will move to the enlarged position unless constrained). In some embodiments, the plurality of walls of the enlargeable section have passive spring action (e.g. will move to the enlarged position unless constrained).

In some embodiments, the multifunctional devices of the present invention comprise a sleeve member. In certain embodiments, the sleeve member encloses at least a portion of the elongate member. In other embodiments, the sleeve member is moveable (e.g. adjustable) between a first position along the elongate member that fully encloses the enlargeable section, and a second position along the elongate member that at most partially encloses the enlargeable section (e.g. at most encloses 95%, 75%, 50%, 25%, 10% or 5% of the enlargeable section). In other embodiments, the enlargeable section is in the non-enlarged position when the sleeve member is in the first position. In particular embodiments, the enlargeable section is in an enlarged position when the sleeve member is in the second position.

In certain embodiments, the sleeve member comprises plastic (e.g., polyethylene, polypropylene, polystyrene, polyvinyl chloride, nylon, polyacetal, polyphenylene oxide, polytetrafluoethylene, polyethylene teraphthalate, polybutylene terephthalate, phenolic urea formaldehyde, melamine formaldehyde, polyester, and combinations thereof).

In other embodiments, the sleeve member is configured to be moved (e.g. adjusted) from outside of a subject's body (e.g. during endoscopic surgery). In some embodiments, the sleeve member comprises a proximal end, and the proximal end is connected to a handle.

In some embodiments, the present invention provides methods for constructing a multifunctional device, comprising; a) providing an elongate member, and b) generating a plurality of openings in the elongate member such that an enlargeable section is formed in the elongate member, wherein the enlargeable section comprises a plurality of walls. In other embodiments, after step b), the elongate member comprises a distal tip. In particular embodiments, the enlargeable section is moveable between a non-enlarged position and an enlarged position, wherein the enlarged position creates a chamber in the elongate member. In particular embodiments, the enlarged position is any position of the enlargeable section that has a cross-sectional dimension greater than the enlarged section when in the non-enlarged position. In certain embodiments, the generating comprises cutting a plurality of holes (e.g. slits) in the elongate member. In some embodiments, the present invention provides methods for constructing a multifunctional device, comprising; generating an elongate member that has a plurality of openings, wherein the plurality of openings form an enlargeable section comprising a plurality of walls. In some embodiments, the generating comprises blow-molding, or otherwise forming, the elongate member such that a plurality of openings are formed therein.

In other embodiments, the present invention provides kits, comprising an elongate member with a plurality of openings defining an enlargeable section, wherein the enlargeable section comprises a plurality of walls, and wherein the enlargeable section is movable between a non-enlarged position, and an enlarged position, wherein the enlarged position forms a chamber in the elongate member, and b) a sleeve member configured for enclosing at least a portion of the elongate member, the sleeve member being moveable between a first position along the elongate member that fully encloses the enlargeable section, and a second position along the elongate member that at most partially encloses the enlargeable section. In other embodiments, the kits of the present invention further comprise any of the additional components of the multifunctional devices mentioned above (e.g. media, inner utility member, adjustment device, elongate member with or without a distal tip, etc.). In certain embodiments, the kits of the present invention further comprise instructions for assembling and/or using the multifunctional devices of the present invention.

In other embodiments, the present invention provides systems, comprising an elongate member with a plurality of openings defining an enlargeable section, wherein the enlargeable section comprises a plurality of walls, and wherein the enlargeable section is movable between a non-enlarged position, and an enlarged position, wherein the enlarged position forms a chamber in the elongate member, and b) a sleeve member configured for enclosing at least a portion of the elongate member, the sleeve member being moveable between a first position along the elongate member that fully encloses the enlargeable section, and a second position along the elongate member that at most partially encloses the enlargeable section. In other embodiments, the systems of the present invention further comprise any of the additional components of the multifunctional devices mentioned above (e.g. media, inner utility member, adjustment device, elongate member with or without a distal tip, etc.). In certain embodiments, the systems of the present invention further comprise instructions for assembling and/or using the multifunctional devices of the present invention.

In other embodiments, the present invention provides multifunctional devices that permit the removal of bodily and irrigation fluids, the injection of irrigation fluids, or the manipulation of tissue (e.g. cautery, cutting, scraping, etc.), comprising an elongate member (e.g. suction and/or irrigation tube) that is connected to, or preferably integral with, an enlargeable section that is configured to provide access down into a surgical field (e.g. for removal or injection of fluids), the enlargeable section defining a chamber volume having an area measured across the elongate member axis similar to the cross-sectional area of the elongate member when the enlarged section is non-deployed (e.g. in a non-enlarged position), and having an area measured across the elongate member axis greater than the cross-sectional area of the elongate member, and thereby an increased chamber volume, when the enlargeable section is deployed (e.g. in an enlarged position).

In some embodiments, the enlargeable section comprises walls. In further embodiments, the wall are perforated. In certain embodiments, the wall of the enlargeable section, when deployed, are capable of pushing bodily tissue outward from the elongate member axis to form an enlarged chamber volume free of bodily tissue (e.g. such that fluids may be collected for removal).

In certain embodiments, the elongate member has a plurality of openings that form the enlargeable area. The openings may be of any shape or size. In some embodiments, the openings are longitudinal, diamond, zig-zag shape, regular, or irregular in shape, and allow adjustment of the chamber shape and volume.

In particular embodiments, the walls of the enlargeable section have passive spring action that opens the enlargeable section to its deployed shape and size. In other embodiments, the walls of the enlargeable section have passive spring action that returns the enlargeable section to its non-deployed (e.g. non-enlarged) shape and size when deployment forces are released or counteracted, whereby the chamber length can be reduced and the chamber width and volume can be increased by pushing on the tube and enlargeable section.

In some embodiments, the multifunctional device further comprises a tissue manipulation tip (including, but not limited to, a cautery tip, scalpel tip, scissors tip, scraping tip, and stitching tip) which can operate both within the enlargeable section and beyond the tip of the enlargeable section.

In further embodiments, the multifunctional device further comprises an adjustment device that connects to the enlargeable section and is operable from the top of the elongate member. In certain embodiments, the adjustment device may be used to change the change length, width and volume (e.g., change the enlargeable section from a non-enlarged position to an enlarged position, or vice versa).

In some embodiments, the multifunctional device of the present invention further comprises a sleeve member around the elongate member, through which the elongate member (e.g. tube) and enlargeable section can move. In certain embodiments, the sleeve member may be used to insert into or withdraw from the surgical area the elongate member (e.g. suction/irrigation tube), with the enlargeable section in a non-deployed (e.g. non-enlarged), or partially deployed condition. In particular embodiments, the sleeve member enclosing at least a portion of the elongate member may be pushed downward around the enlargeable section to transfer the location of maximal suction and/or irrigation forces toward the proximal end of the device.

In certain embodiments, the walls of the enlargeable section comprise tynes. In some embodiments, when the tynes are spread apart form openings between them for fluid movement. In particular embodiments, the tynes have outward or inward passive spring action to create deployment or non-deployment forces.

In some embodiments, the multifunctional device of the present invention comprises flexible media material surrounding and/or conforming to at least a portion of the enlargeable section. In certain embodiments, the flexible media serves to control movement of materials into the chamber. In other embodiments, the media is fluid permeable or impermeable, or perforated, in specific areas, thus restricting bodily tissue from entering the chamber.

In additional embodiments, the multifunctional device further comprises an inner utility member (e.g. suction and/or irrigation tube) inside of the elongate member. The inner suction/irrigation tube may be employed to additionally remove bodily or irrigation fluids or inject irrigation fluids. In other embodiments, the insertion depth of the inner suction/irrigation tube determines the zone from which fluids are removed or to which fluids are injected within the chamber.

DEFINITIONS

Figure 1:
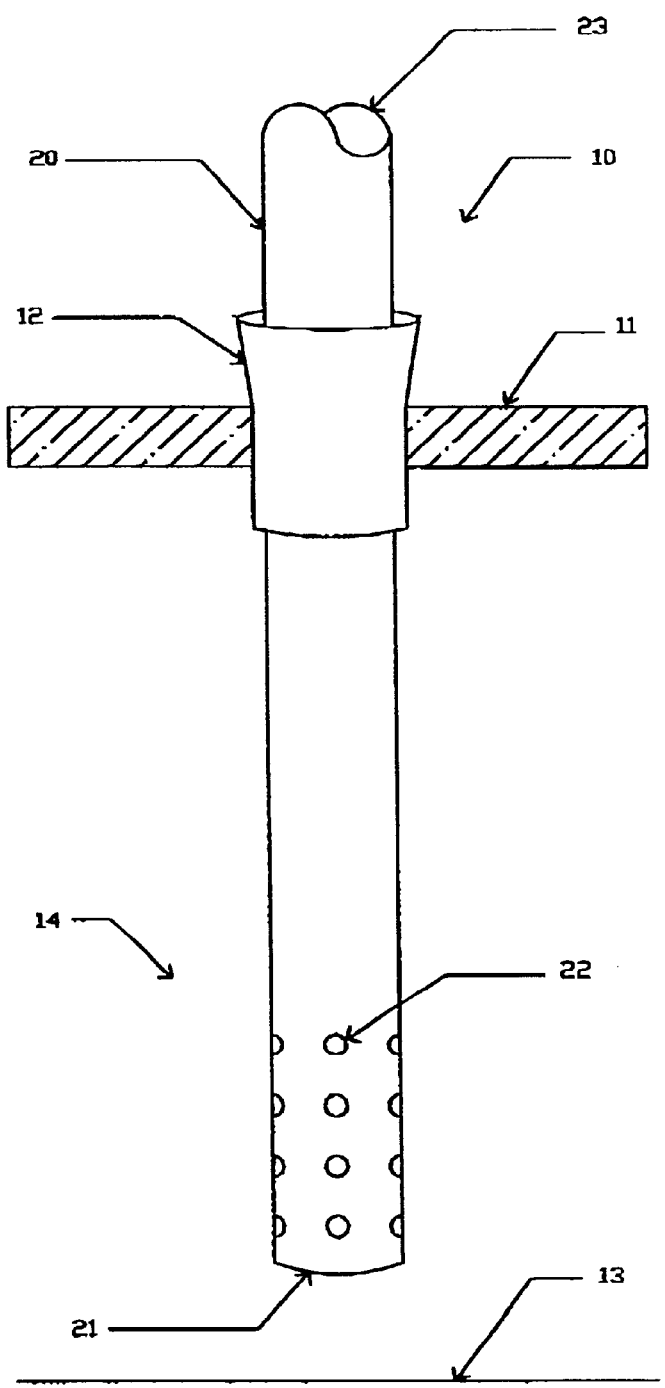
FIG. 1 shows a cutaway perspective view of a prior art endoscopic surgery suction device.

To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited to, individuals requiring surgery, and in particular, requiring endoscopic surgery for diagnostic or therapeutic purposes.

As used herein, the terms "endoscopic surgery" and "endoscopic procedures", and like terms, refer to what is generally known as laproscopic or endoscopic surgery, which generally involves indirect visualization of the operative field with a small camera (e.g. specialized fiberoptic telescopes measuring less than a half inch in diameter that are attached to high resolution television cameras). Endoscopic surgery is generally done by way of multiple small incisions through which a camera and instruments are inserted. The instruments perform their functions inside the body but are operated by use of their handles outside the body. Examples of endoscopic surgery include endoscopic appendix or gallbladder removal.

As used herein, the term "primary cross-sectional dimension" when used in reference to the elongate member, refers the cross sectional dimension (i.e. area of the internal opening) in the elongate member that is present throughout at least 50% of the length of elongate member (i.e. at least 50% of the length of the elongate member has a cross-sectional dimension that is the same value, referred herein as the primary cross-sectional dimension). In some embodiments, the primary cross-sectional dimension is present throughout at least 60%, or at least 70%, or at least 80%, or at least 90%, or at least 95% of the elongate member. In preferred embodiments, the primary cross-sectional dimension is present throughout about 100% of the elongate member (e.g. a tube of approximately uniform diameter is employed).

As used herein, the term "distal tip" when used in reference to a portion of the elongate member, refers to the area of the elongate member that is distal of the enlargeable section of the elongate member. In some embodiments, the distal tip has approximately the same cross-sectional dimension as the primary cross-sectional dimension of the elongate member. In other embodiments, the distal tip is non-enlargeable.

GENERAL DESCRIPTION OF THE INVENTION

The present invention relates generally to multifunctional devices for performing suction, irrigation, and manipulation at an internal site in a subject, and more particularly to enlargeable multifunctional devices for performing such functions while avoiding obstruction during conventional and endoscopic surgery.

The present invention eliminates many of the problems associated with malleable tissue obstruction or impeding suction catheters, irrigation catheters, and other surgical instruments. The present invention permits conventional utilization of suction, irrigation, and other functions, but also provides the ability to deploy and retract a guard (e.g. enlargeable section) to create an area (e.g. chamber) free of tissue interference. The tissue guard (enlargeable section) may be activated (e.g. go from non-enlarged position to an enlarged position), for example, by direct pressure of the device tip against tissue (or other firm surface). The tissue guard (enlargeable section) may also be activated, for example, by a mechanism on the device handle or passive spring action. When the enlargeable section is deployed (e.g. in an enlarged position), it forms a barrier preventing tissue from coming into direct contact with any functioning portion of the device (e.g. suction, irrigation, or tissue manipulation part of the device).

In preferred embodiments, the multifunctional devices of the present invention comprise an elongate member (e.g. a hollow tube) with longitudinal slits or other perforations/openings that run to nearly the end of the elongate member (e.g. a plurality of openings are formed near the distal end of the elongate member forming an enlargeable section adjacent to the distal tip of the elongate member). In other embodiments, the multifunctional devices of the present invention comprise an elongate member (e.g. hollow tube) with longitudinal or other perforations/opening that run to the end of the elongate member (e.g. a plurality of openings are formed at the distal end of the elongate member forming an enlargeable section at the end of the elongate member).

Also in preferred embodiments, when the tip (e.g. very end) of the elongate member is forced against an object or is pulled proximally toward the top of the elongate member (e.g. toward the handle), the openings (e.g. slits, perforations, etc) allow the sides of the elongate member (e.g. the walls of the enlargeable section of the elongate member) to bow out. This creates a cavity (e.g. chamber) that is protected from tissue encroachment by the bowed-out walls. In certain embodiments, the multifunctional devices have a suctioning function, and the formation of the chamber (e.g. when the enlargeable section is in the enlarged position) causes the suction interface to shift from the area just beyond the distal tip of the elongate member, to the an area within the enlargeable section, or just above the enlargeable section.

Since the multifunctional devices of the present invention may be moved between a non-enlarged position and an enlarged position (e.g. the enlargeable section of the elongate member may be in enlarged and non-enlarged positions), the device may be inserted through openings otherwise too small to accommodate a device with bowed out chambers. In this regard, the devices of the present invention may be used in a conventional manner, or passed through introducer ports (e.g. for endoscopic type surgery), by reversing the bowing process, thus causing the cross-sectional dimension of the enlargeable section to return to "normal" (e.g., return to a position such that the enlargeable section has approximately the same cross-sectional dimension as the primary cross-sectional dimension of the elongate member).

DETAILED DESCRIPTION OF THE INVENTION

The multifunction devices of the present invention have advantages over previous prior art devices. FIG. 1 shows a prior art suction device, and FIGS. 2–5 show various preferred embodiments of the multifunctional devices of the present invention.

Referring to FIG. 1, a prior art suction device 10 penetrates the body wall 11 of a subject through an introducer 12 down to the surgical field 13 where bodily and irrigation fluids 14 accumulate. Tube 20 transmits fluids during surgery through hole 21 (not shown, and not always present) in the tube 20 end, and holes 22 in the tube 20 sides from the surgical area inside the body 14 to outside the body 23.

Referring generally to FIGS. 2, 3, 4, and 5, elongate member 20 (e.g. suction/irrigation tube) is connected to, or preferably integral with, an enlargeable section 30 (i.e. elongate member 20 has an enlargeable section 30). Elongate member 20 allows removal of bodily fluids and irrigation fluids during surgical operations inside the bodies of subjects (e.g. humans and other animals, such as cows, pigs, horses, dogs, cats, and other mammals). The enlargeable section 30 may be in a non-enlarged (non-deployed) position or an enlarged (deployed) position. FIGS. 2, 3, 4 and 5 show the enlargeable section 30 in an enlarged position. Generally, the enlargeable section 30, when in the non-deployed position, is of similar cross-sectional dimension 31 as elongate member 20, but when in a deployed position, is of a cross-sectional dimension, such as 32, that is larger than the cross-sectional dimension 31 of elongate member 20.

Figure 2:
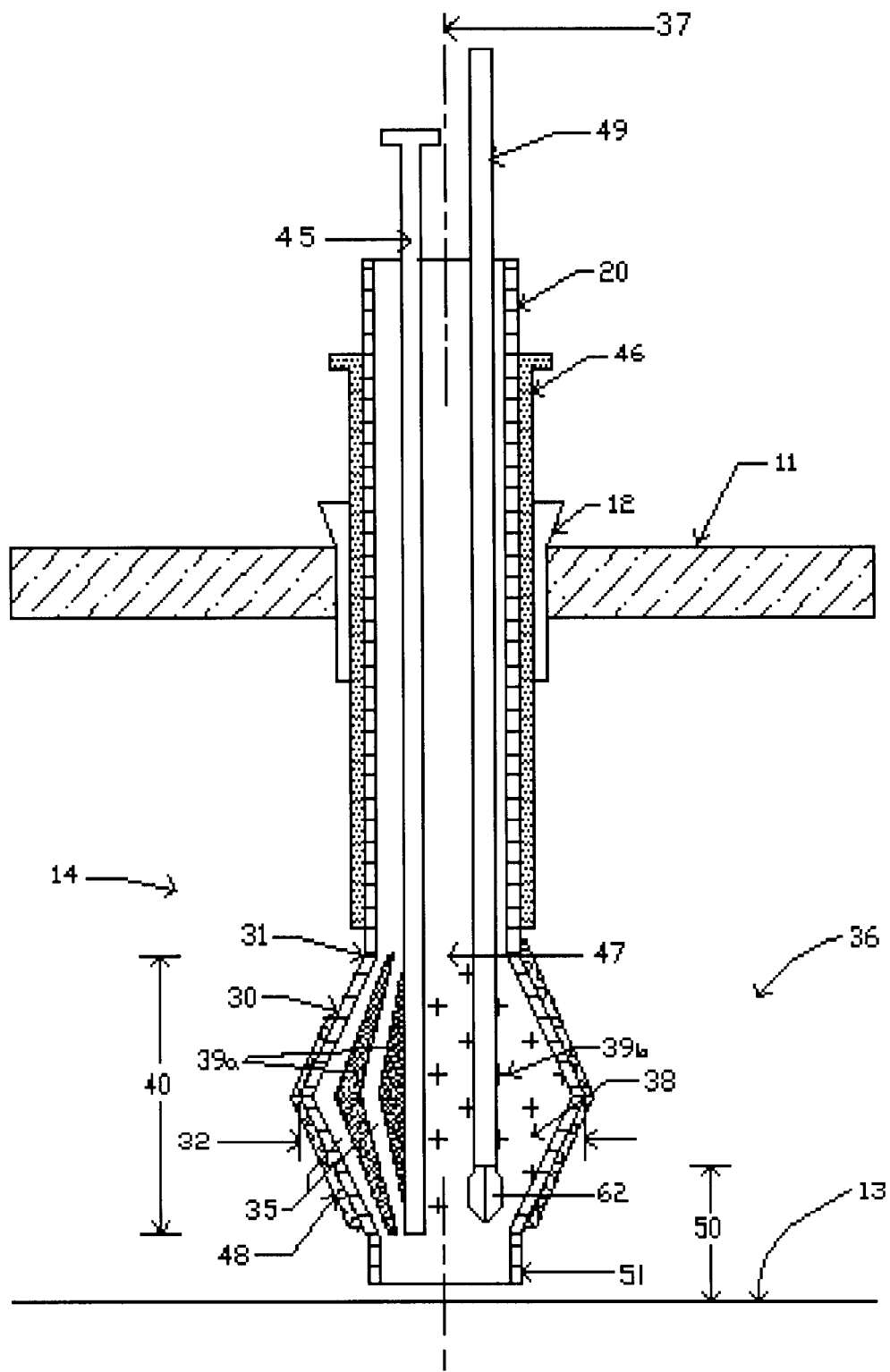
FIG. 2 shows one embodiment of the multifunctional device of the present invention.
Figure 5:
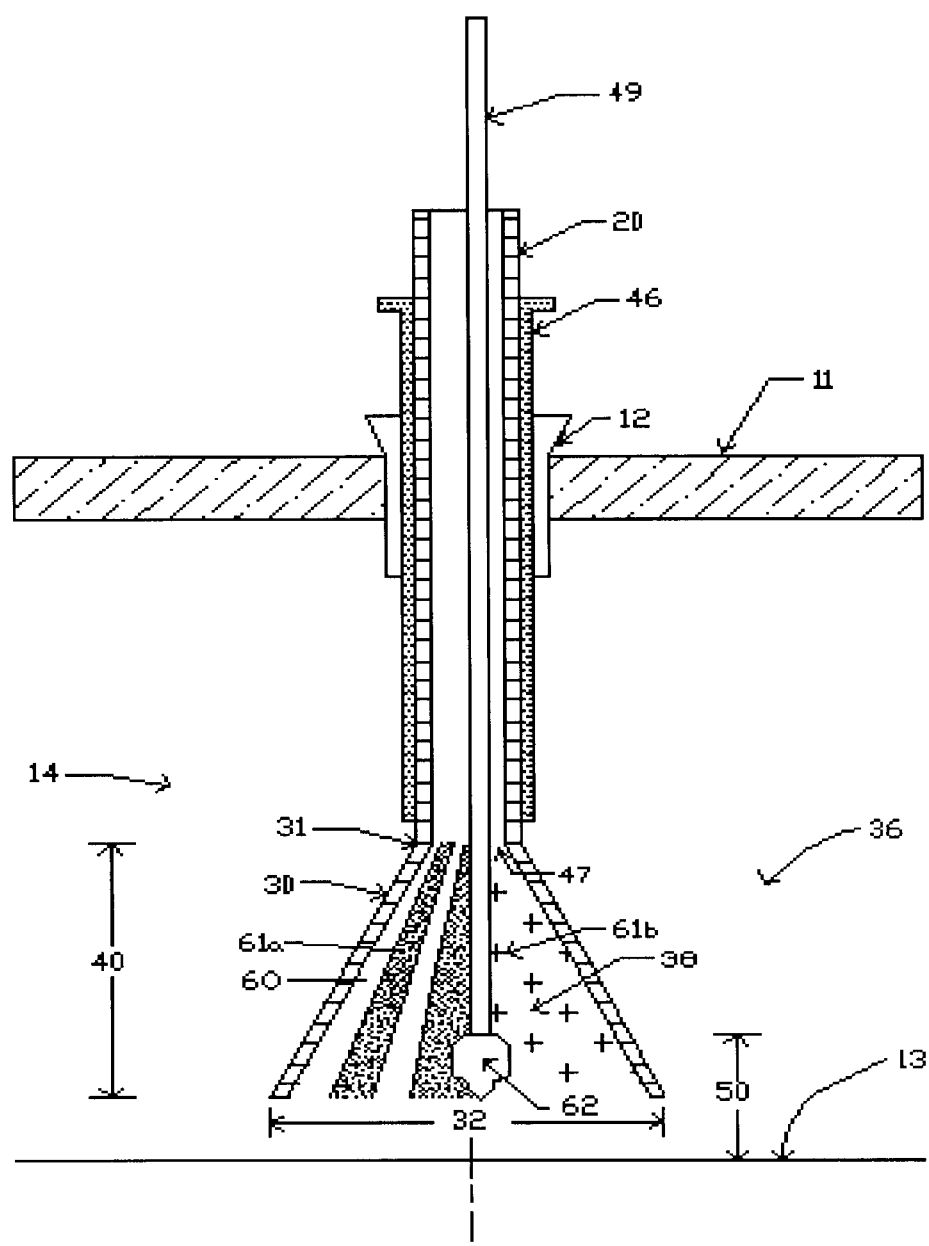
FIG. 5 shows a further embodiment of the multifunctional device of the present invention.

In particularly preferred embodiments, the walls 35 of deployed enlargeable section 30 are capable of pushing bodily tissue 36 (e.g. malleable tissue) outward away from the elongate member 20 axis 37, and form a chamber 38. In certain embodiments, the enlargeable section contains a plurality of openings 39. FIGS. 2 and 5 show "slit" type openings 39a, between walls 35. In some embodiments, the slit openings are longitudinal (e.g. 39a), horizontal, angled, or combinations thereof. FIGS. 2 and 5 also show an alternative embodiments with openings 39b (e.g. perforations) cut in a zig-zag pattern (e.g. to form an expanding mesh). In certain embodiments with perforations 39b, the perforations may be any type of opening, including, but not limited to, longitudinal, diamond, regular or irregular shaped openings. Openings 39 (e.g. 39a and 39b) may allow adjustment of the chamber shape and volume.

The chamber 38 shape and volume may be varied by adjusting its length 40 and width 32. The chamber 38 length 40 can be decreased and the chamber 38 width 32 can be increased, for example, by pushing elongate member 20 downward against the surgical field 13. This motion may also act to bring the point of maximum suction 47 closer to the surgical field 13.

The walls 35, in some embodiments, have inward passive spring action that returns the enlargeable section 30 to its non-deployed (non-enlarged) shape and size when deployment forces are released or counteracted. In alternative embodiments, the plurality of walls 35 have outward passive spring action that opens the enlargeable section 30 to its deployed shape and size of variable length 40 and width 32.

Adjustment device 45, which connects to the bottom of enlargeable section 30 and is operable from the top of elongate member 20, can be used to change the chamber 38 length 40 and width 32. Adjustment device 45 can be used to increase or decrease the volume of chamber 38.

Sleeve member 46, which surrounds elongate member 20, can be used for many purposes. For example, for device insertion purposes, with enlargeable section 30 non-deployed and retracted within sleeve member 46, the enlargeable section 30 and elongate member 20 can be inserted into the surgical area. After insertion, sleeve member 46 can be partially pulled back such that walls 35, when including outward passive spring action, will open to form enlarged chamber dimension 32. In another example of employing sleeve member 46, for device removal purposes, sleeve member 46 can be used to reduce the enlargeable section 30 width 32 to the same cross-sectional area 31 of elongate member 20 for removal of enlargeable section 30 and elongate member 20 through sleeve 46. In a further example, for controlled suction and irrigation purposes, sleeve member 46 can be pushed toward the surgical field 13. Through this downward movement, sleeve member 46 compresses the walls 35 inward from the larger dimension 32 to the smaller dimension 31, blocks increasing percentages of the openings 39, and thereby transfers the location of maximal suction or irrigation forces 47 downward toward the surgical field 13.

Media 48 may surround part or all of enlargeable section 30 to control movement of materials into chamber 38. Media 48 is flexible to conform to the variable shape of walls 35. Specific areas of media 48 may be permeable or impermeable to fluids, and may further contain perforations. Media 48 restricts bodily tissue from entering chamber 38 (e.g. restricts bodily tissue from entering openings 39).

Inner utility member 49 (e.g. suction/irrigation tube or tissue manipulation support), inserts into elongate member 20 and chamber 38 as an additional or alternative means for removal of bodily and irrigation fluids, or as a tissue manipulation support (e.g. for attaching a tissue manipulator tip). The depth of insertion determines the zone from which fluids are removed. As insertion depth increases and dimension 50 therefore decreases, fluid levels are lowered closer to surgical field 13. Tissue manipulator tip 62 may be attached to, or integral with, inner utility member 49 (e.g. in order to perform surgical maneuvers, such as cutting, cauterizing, knot tying, scraping, and stitching).

Figure 3:
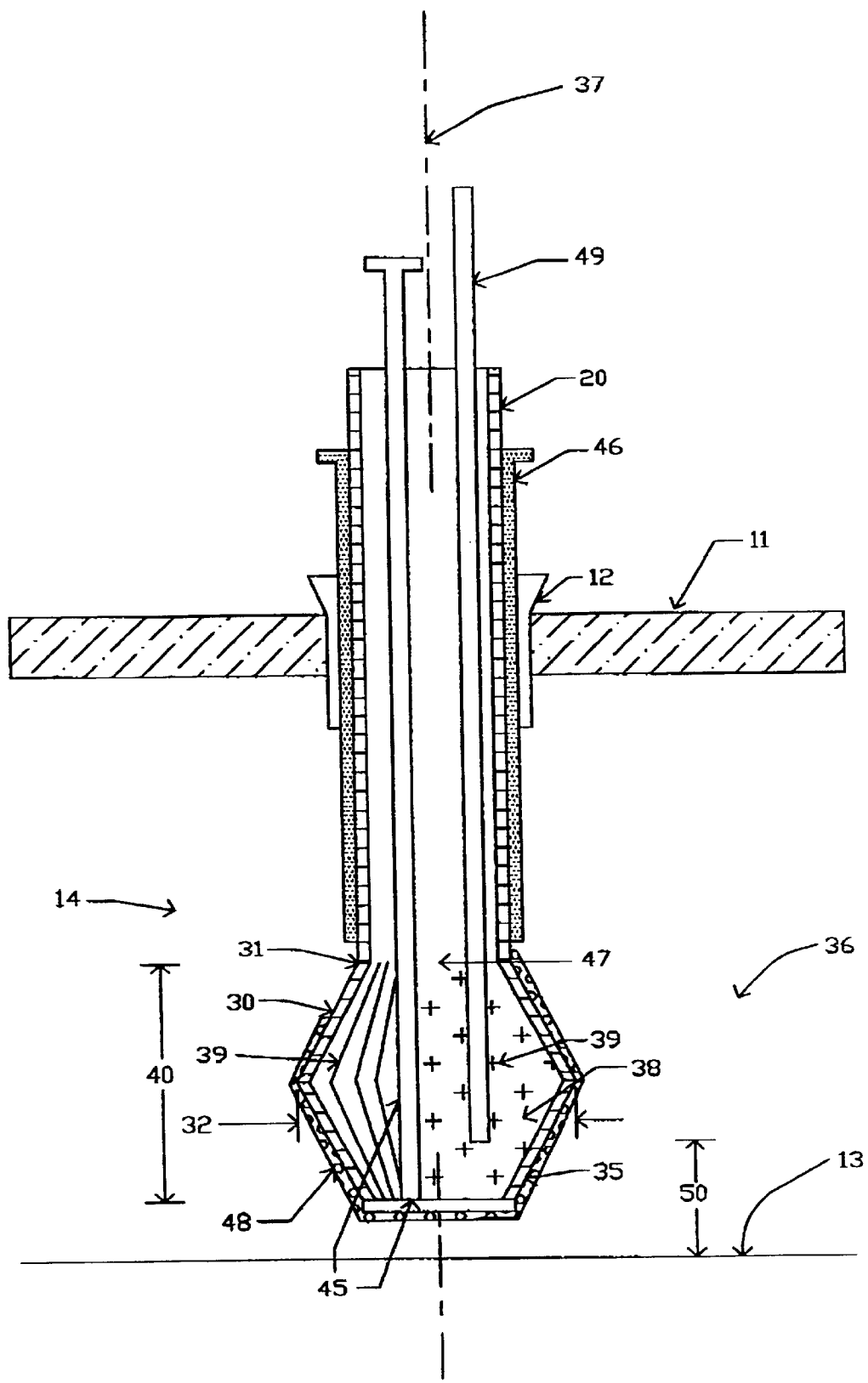
FIG. 3 shows another embodiment of the multifunctional device of the present invention.

Referring now to FIGS. 2 and 3 specifically, both of these figures show the enlargeable section 30 in an enlarged position such that a 'bulging midsection' is formed (i.e. enlargeable section 30 is narrower at either end, and larger in the middle). In preferred embodiments, the cross-sectional dimension adjacent to both ends of the enlargeable section 30 is approximately the same (e.g. approximately the same cross-sectional dimension as the primary cross-sectional dimension of the elongate member 20). FIG. 2 specifically shows a distal tip 51 of elongate member 20 adjacent to the enlargeable section 30 that has approximately the same cross-sectional dimension as elongate member 20. FIG. 2 also shows a tissue manipulation tip 62 at the end of inner utility member 49.

Figure 4:
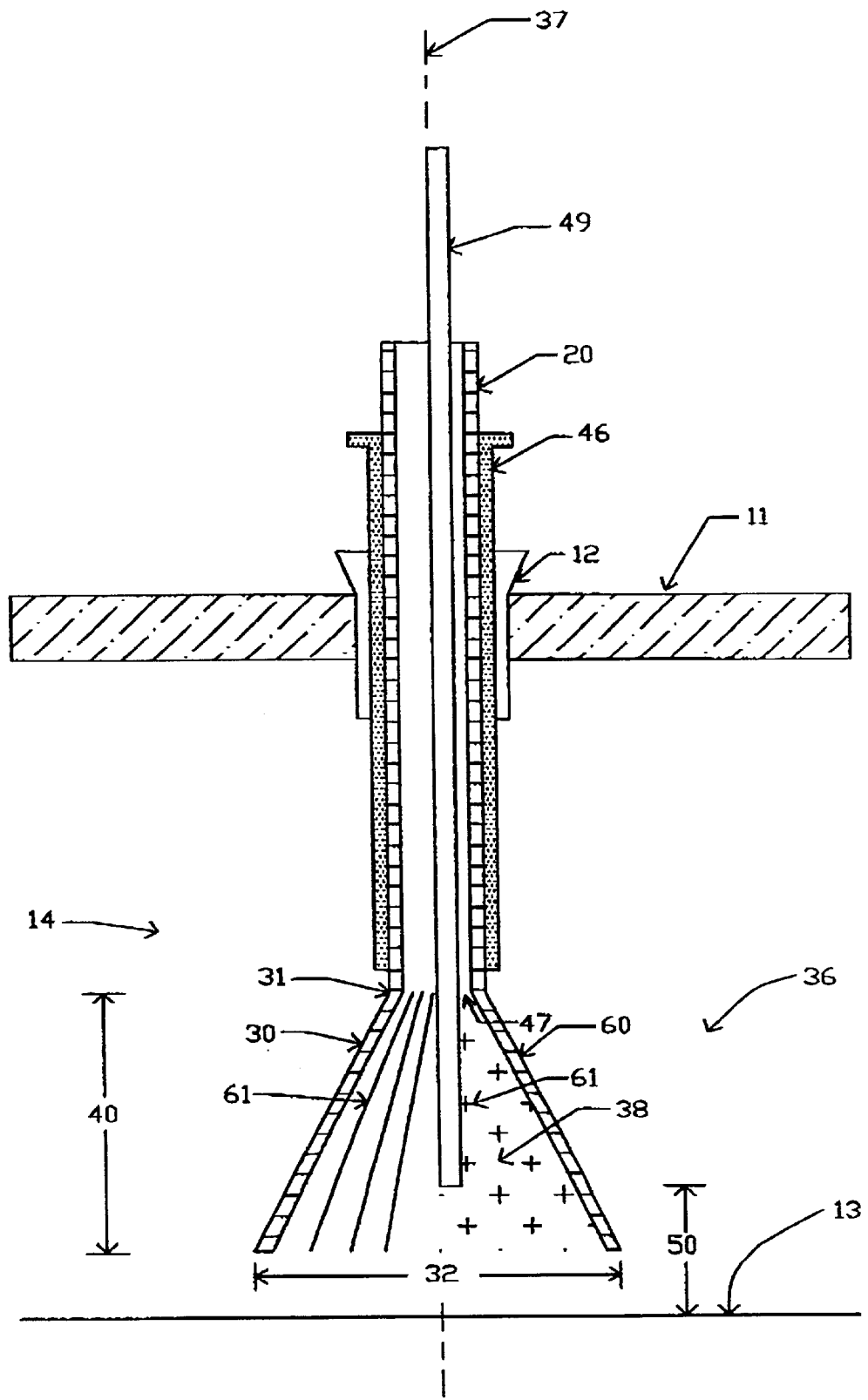
FIG. 4 shows an additional embodiment of the multifunctional device of the present invention.

Referring now to FIGS. 4 and 5 specifically, both of these figures show the enlargeable section 30 in an enlarged position such that a 'cone configuration' is formed (i.e. enlargeable section 30 is narrower at one end (approximately the same cross sectional dimension as elongate member 20), and the other end is the widest part of the enlargeable section 30. FIG. 5 also shows a tissue manipulation tip 62 at the end of inner utility member 49.

The multifunctional devices of the present invention have many advantages. For example, in certain embodiments, the enlargeable section may be constructed by cutting holes (e.g. longitudinal slits) in an existing elongate member, instead of attaching a separate enlargeable member to an elongate member. In this regard, the devices of the present invention are reliable (e.g. few parts) and easy to produce (e.g. no extra steps to create and attach a separate enlargeable member). Another advantage of the devices of the present invention is that, in many embodiments, there are no tynes (or other potentially dangerous protuberances) that stick out that could damage tissue (e.g. embodiments with a "bulging midsection" do not have tynes sticking out that might damage tissue). Furthermore, in some embodiments, the walls of the enlargeable section and/or the media (membrane) surrounding the enlargeable section, prevents tissue from being blocking the ability of the multifunctional devices to provide a suction, irrigation, or tissue manipulation function.

The enlargeable section of the present invention can be continuously enlarged to different sizes or can have various predetermined sizes in the deployed (expanded position). The walls of the enlargeable section can have various predetermined or preformed configurations or shapes in the expanded position in accordance with procedural use including various shapes for holding back or manipulating tissue and defining or circumscribing various working or operating spaces. Some configurations for the enlargeable section that are particularly advantageous include, but are not limited to, "bulging midsection" configurations, "cone-shaped" configurations", triangular, oval, single or multiple ball-shaped, etc. Any shape that that creates space during surgery, or allows irrigation or suction to occur without blockage are useful in the present invention.

The multifunctional devices of the present invention are useful for performing conventional surgery. Examples of conventional surgery include, but are not limited to, abdominal surgeries, urologic surgeries, gynecologic surgeries, thoracic surgeries, cardiac surgeries, and vascular surgeries. The multifunctional devices are also useful for conventional microsurgeries (e.g. of the hand), peripheral vascular surgeries, neurosurgery (e.g. peripheral, spinal cord, and intracranial), and otolaryngological (ENT) surgeries.

The multifunctional devices of the present invention are particularly useful for endoscopic type procedures. Examples of procedures in which the devices of the present invention may be employed include, but are not limited to, laparoscopic cholecystectomy, laparoscopic treatment of gastroesophageal reflux and hiatal hernia, laparoscopic cardiomyotomy (Heller Myotomy), laparoscopic gastrostomy, laparoscopic vagotomy, laparoscopic plication of perforated ulcer, gastric resections, laparoscopic bariatris surgery, small bowel resections, enterolysis, enteroenterostomy, placement of jejunostomy tube, laparoscopic appendectomy, laparoscopic colostomy, laporoscopic segmental colectomies, anterior resections, abdominopereneal resection, laparoscopic-assisted proctocolectomy, distal pancreatectomy, laparoscopic cholecystojejunostomy, laporoscopic gastrojejunostomy, laporoscopic splenectomy, lymph node biopsy, laparoscopic adrenalectomy, laproscopic inguinal hernia repair, laproscopic repair of ventral hernia, upper gastrointestinal endoscopy, small bowel enteroscopy, endoscopic retrograde cholangiopancreatography, choledochostomy, flexible sigmoidoscopy, colonoscopy, and pediatric endoscopy. These and other techniques and methods suitable for use with the multifunctional devices of the present invention are described in "The Sages Manual, Fundamentals of Laparoscopy and GI Endoscopy", edited by Carol E. H. Scott-Conner, Spinger Pub., 1999, herein specifically incorporated by reference.

All publications and patents mentioned in the above specification are herein incorporated by reference. Various modifications and variations of the described devices, compositions, methods, systems, and kits of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in art are intended to be within the scope of the following claims.

We claim:

1. A multifunctional device configured for performing at least one function at an internal site in a subject, comprising;
   a) a tube comprising;
      i) a plurality of openings defining an enlargeable section in said tube, wherein said enlargeable section is movable between a non-enlarged position, and an enlarged position, wherein said enlarged position forms a chamber in said tube, and
      ii) a distal tip, wherein said distal tip is adjacent to said enlargeable section, and wherein said distal tip is attached to said enlargeable section; and
      wherein said tube configured such that fluid transmitted through said tube contacts both the inner surface of said enlargeable section and the inner surface of said distal tip; and
   b) an inner utility member, wherein said inner utility member comprises a proximal end and a distal end, and wherein said inner utility member is disposed inside said tube such that there is a gap between said inner utility member and said tube along the entire inner surface of said tube, and
   c) a tissue manipulation tip comprising a proximal end and a distal end, wherein said proximal end of said tissue manipulation tip is attached to said distal end of said inner utility member.

2. The device of claim 1, wherein at least one of said plurality of openings is a longitudinal opening.

3. The device of claim 1, wherein said at least one function is selected from suctioning, irrigation, and tissue manipulation.

4. The device of claim 1, wherein said tube comprises plastic.

5. The device of claim 1, wherein at least a portion of said enlargeable section is enclosed by media.

6. The device of claim 1, further comprising an adjustment device, wherein at least a portion of said adjustment device is within said tube.

7. The device of claim 1, wherein said tissue manipulation tip is selected from the group consisting of a cautery tip, a scalpel tip, a scissors tip, a scraping tip, and a stitching tip.

8. The device of claim 1, wherein the diameter of said tube is between 4 mm and 10 mm.

9. The device of claim 1, wherein enlargeable section has passive spring action configured to move said enlargeable section to said enlarged position unless constrained.

10. A multifunctional device configured for performing at least one function at an internal site in a subject, comprising;
    a) a tube comprising
       i) a plurality of openings defining an enlargeable section in said tube, wherein said enlargeable section is movable between a non-enlarged position, and an enlarged position, wherein said enlarged position forms a chamber in said tube, and
       ii) a distal tip, wherein said distal tip is adjacent to said enlargeable section, and wherein said distal tip is attached to said enlargeable section; and
       wherein said tube is configured such that fluid transmitted through said the contacts both the inner surface of said enlargeable section and the inner surface of said distal tip; and
    b) a sleeve member enclosing at least a portion of said tube, said sleeve member being moveable between:
       i) a first position along said tube that fully encloses said enlargeable section such that said enlargeable section can only be in said non-enlarged position when said sleeve member is in said first position, and
       ii) a second position along said tube that at most partially encloses said enlargeable section such that said enlargeable section is in said enlarged position when said sleeve member is in said second position.

11. The device of claim 10, wherein at least a portion of said enlargeable section is enclosed by media.

12. The device of claim 10, wherein said at least one function is selected from suctioning, irrigation, and tissue manipulation.

13. The device of claim 10, wherein said enlargeable section has passive spring action configured to move said enlargeable section to said enlarged position unless constrained.

14. The device of claim 10, wherein said tube comprises plastic.

15. The device of claim 10, wherein the diameter of said tube is between 4 mm and 10 mm.

* * * * *